United States Patent [19]

Sauers et al.

[11] Patent Number: 5,326,834

[45] Date of Patent: Jul. 5, 1994

[54] AUTOCLAVABLE CONTAINERS COMPRISING POLY(ARYL ETHER SULFONES) HAVING ENVIRONMENTAL STRESS-CRACK RESISTANCE

[75] Inventors: Marvin E. Sauers, Flowery Branch; Barry L. Dickinson, Alpharetta, both of Ga.

[73] Assignee: Amoco Corporation, Chicago, Ill.

[21] Appl. No.: 68,241

[22] Filed: May 27, 1993

Related U.S. Application Data

[63] Continuation-in-part of Ser. No. 806,488, Dec. 13, 1991, abandoned, which is a continuation of Ser. No. 163,781, Mar. 3, 1988, abandoned.

[51] Int. Cl.$^5$ .................. C08G 75/02; C08L 81/06
[52] U.S. Cl. .................. 525/534; 525/535; 525/537; 528/174
[58] Field of Search .................. 525/534, 535, 537; 528/174

[56] References Cited

U.S. PATENT DOCUMENTS

| | | | |
|---|---|---|---|
| 4,273,903 | 6/1981 | Rose | 525/534 |
| 4,654,410 | 3/1987 | Kashiwame et al. | 528/174 |
| 4,755,556 | 7/1988 | Harris et al. | 524/609 |
| 5,086,130 | 2/1992 | Dickinson et al. | 525/535 |
| 5,164,466 | 11/1992 | El-Hibri et al. | 525/537 |

*Primary Examiner*—John C. Bleutge
*Assistant Examiner*—Helen F. Lee
*Attorney, Agent, or Firm*—Richard J. Schlott; Stephen L. Hensley

[57] ABSTRACT

An autoclavable container comprising a poly(aryl ether) resin capable of withstanding at least 1000 cycles of steam sterilization at a stress level of 500 psi without stress-crack failure, said steam sterilization cycle conducted for 30 min. at 270° F. and 27 psi using aqueous morpholine at a concentration of 50 ppm.

3 Claims, No Drawings

AUTOCLAVABLE CONTAINERS COMPRISING POLY(ARYL ETHER SULFONES) HAVING ENVIRONMENTAL STRESS-CRACK RESISTANCE

CROSS-REFERENCE TO RELATED APPLICATIONS

This application is a continuation-in-part of U.S. application Ser. No. 07/806,488, filed Dec. 13, 1991, which was a continuation of U.S. application Ser. No. 07/163,781, filed Mar. 3, 1988, both now abandoned.

BACKGROUND OF THE INVENTION

This invention is directed to the use of certain well-defined poly(aryl ether surfones) in medical devices where transparency and excellent environmental stress-crack resistance are required. These poly(aryl ether sulfones) are based on 4,4'-dichlorodiphenyl sulfone and 4,4'-biphenol, optionally including one or more additional dihydroxy compounds selected from 4,4'-dihydroxydiphenyl sulfone, hydroquinone and 2,2'bis(4-hydroxyphenyl)propane (bisphenol-A).

Articles made from these poly(aryl ether sulfones) can be stem-sterilized while under stresses of 500 psi or greater, moreover, they are not affected by corrosion-reducing additives such as morpholine, for example. Also, the above materials demonstrate good chemical resistance in contact with commonly used hospital cleaners and detergents.

Poly(aryl ether sulfones) have been known for about two decades. They are tough linear polymers that possess a number of attractive features such as excellent high temperature resistance, good electrical properties, and very good hydrolytic stability. Commercially available poly(aryl ether surfones) include the polycondensation product of 4,4'-dihydroxydiphenyl sulfone with 4,4'-dichlorodiphenyl sulfone, described in, for example, Canadian Patent No. 847,963. The polymer, available from Imperial Chemical Industries, Ltd. contains no aliphatic moieties and has a heat deflection temperature of approximately 210° C. Another commercial poly(aryl ether sulfone), available from Amoco Performance Products, Inc. under the trademark of UDEL ®, has a heat deflection temperature of about 180° C. and may be made via the nucleophilic polycondensation of bisphenol-A di-sodium salt with 4,4'-dichiorodiphenyl sulfone, as describe in U.S. Pat. No. 4,108,837.

Over the years, there has developed a substantial body of patent and other literature directed to the formation and properties of poly(aryl ether sulfones) and other poly(aryl ethers) (all hereinafter called "PAE"). A broad range of PAE's was achieved by Johnson et al., J. of Polymer Science, A-1, Vol. 5, 1967, pp. 2415-2427; Johnson et al., U.S. Pat. Nos. 4,108,837 and 4,175,175. Johnson et al. show that a very broad range of PAE's can be formed by the nucleophilic aromatic substitution (condensation) reaction of an activated aromatic dihalide and an aromatic diol. By this method, Johnson et al. created a host of new PAE's.

Because of their excellent mechanical and thermal properties, coupled with outstanding hydrolytic stability, the poly(aryl ether sulfones) have been utilized in the medical market for a variety of purposes for at least ten years. These medical devices constitute a wide variety of articles. Obviously, one of the major attributes of these resins that contributes to their wide acceptance for these uses is their ability to be steam autoclaved repeatedly without loss of properties. Steam autoclaving exposes these articles to very severe stresses, and involves repetitive exposures to wet/dry and hot/cold cycles.

Copolymers of 4,4'-dichlorodiphenyl sulfone and 4,4'-dihydroxydiphenyl sulfone together with 4,4'-biphenol are described in British Patent Application No. 2,088,396. The copolymers comprise about 80 to 10 mole percent of repeat units derived from 4,4'-dihydroxydiphenyl sulfone, and correspondingly about 20 to 90 mole percent of repeat units derived from 4,4'-biphenol The application states that the incorporation of the units derived from 4,4'-biphenol into the poly(aryl ether sulfone) yields materials with improved resistance to hot water crazing. The application does not mention steam-sterilizability under load, nor does it teach that the copolymers show resistance to stress-cracking in the presence of boiler additives such as morpholine, or when in contact with typical hospital cleaners and detergents.

Poly(aryl ether sulfones) such as the commercially-available resins described previously show some important deficiencies, particularly in steam sterilization. Parts molded from these materials may stress-crack when stem sterilized under stresses of, say, 500 psi or greater. Where boiler additives such as morpholine are employed to reduce corrosion in the stem generating system or when in contact with commonly used hospital cleaners and detergents, these materials are particularly subject to stress-crack failure. The deficiencies are particularly important when the molded article will be subjected to frequent sterilizations during use, such as in medical storage trays and containers for use in sterilizing and storing medical instruments or the like. Medical appliances, including prostheses dental appliances, implantable devices and the like wherein prolonged contact with tissue is envisioned, are generally sterilized by alternative means, in part to avoid introducing possible contaminants. In addition, such medical appliances are not subjected to routine cleaning with detergents or the like. Inasmuch as these articles thus ordinarily will not encounter the extreme stresses imposed by cleaning and steam sterilization, the prior art resins generally suffice for these applications.

An improved resin capable of withstanding repeated stem sterilization without stress-cracking or similar failure would thus be an important improvement, particularly for use in the production of steam-sterilizable medical storage trays and containers.

THE INVENTION

The instant invention is an autoclavable container or storage tray particularly useful for storage and delivery of sterile surgical instruments. The autoclavable containers are capable of withstanding 1000 cycles of stem sterilization at a stress level of at 500 psi for at least 1000 cycles, when conducted at 270° F. under a pressure of 27 psi using aqueous morpholine at a concentration of 50 ppm, and thus will be capable of being autoclaved together with the surgical instruments, thereby avoiding the need for providing sterile wrapping and the costs associated therewith. The containers may also find acceptance in the medical supply industry for shipment and storage of sterile implants, prostheses and other medical devices under sterile conditions and in many other similar applications.

Certain poly(aryl ether sulfones) display superior stress-crack resistance when steam-sterilized under stresses of 500 psi or greater. These materials are unaffected by corrosion-reducing additives in the stem generating system (e.g., by morpholine or similar substances) or when in contact with commonly used hospital cleaners and detergents. Storage trays and containers comprised of such poly(aryl ether sulfone) resins are autoclavable.

The poly(aryl ether sulfones) of the instant invention are polymers of 4,4'-dichlorodiphenyl sulfone with 4,4'-biphenol, optionally including up to about 40 mole % of 4,4'-dihydroxydiphenyl sulfone. The polymers may be further described as consisting of from 60 to about 100 mole% of the structural unit:

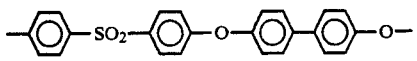

and, correspondingly, from 40 to 0 mole % of the structural unit:

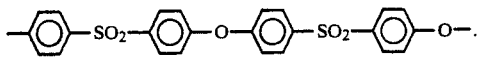

The poly(aryl ether sulfones) may be prepared by either of two methods, known widely in the resin art as the carbonate method and the alkali metal hydroxide method.

In the carbonate method, the polymers are prepared by contacting substantially equimolar amounts of the hydroxy-containing compounds and dihalodiarylsulfones, e.g., 4,4'-dichlorodiphenyl sulfone or 4,4'-difluoro-diphenyl sulfone, with from about 0.5 to about 1.0 mole of an alkali metal carbonate per mole of hydroxyl group in a solvent mixture comprising a solvent which forms an azeotrope with water in order to maintain the reaction medium at substantially anhydrous conditions during the polymerization.

The temperature of the reaction mixture is kept at about 170° C. to about 250° C., preferably from about 210° C. to about 235° C., for about one to 15 hours. The reaction is carried out in an inert atmosphere, e.g., nitrogen, at atmospheric pressure, although higher or lower pressures may also be used. The polyarylethersulfone is then recovered by conventional techniques such as coagulation, solvent evaporation, and the like. The solvent mixture comprises a solvent which forms an azeotrope with water and a polar aprotic solvent.

The solvent, which forms an azeotrope with water, includes an aromatic hydrocarbon such as benzene, toluene, xylene, ethylbenzene, chlorobenzene, and the like. The polar aprotic solvents employed in this invention are those generally known in the art for the manufacture of polyarylether sulfones and include sulfur-containing solvents such as dialkyl sulfoxides, dialkyl sulfones, diarylsulfones, cycoaliphatic sulfones and the like, as well as nitrogen-containing polar solvents such as dimethylacetamide, dimethylformamide, N-methylpyrrolidone and the like. The azeotrope-forming solvent and polar aprotic solvent are used in a weight ratio of from about 1:10 to about 1:1, preferably from about 1:5 to about 1:3.

It is essential that the reaction medium be maintained substantially anhydrous during the polycondensation. While amounts of water up to about one percent can be tolerated, and are somewhat beneficial when employed with fluorinated dihalobenzenoid compounds, amounts of water substantially greater than this are desirably avoided as the reaction of water with the halo and/or nitro compound leads to formation of phenolic species and only low molecular weight products are secured. Consequently, in order to secure the high polymers, the system should be substantially anhydrous, and preferably contain less than 0.5 percent by weight water during the reaction.

Preferably, after the desired molecular weight has been attained, the polymer is treated with an activated aromatic halide or an aliphatic halide such as methyl chloride or benzyl chloride, and the like, to convert the terminal hydroxyl groups into ether groups and stabilize the polymer. The polymer so treated has good melt and oxidative stability.

While the carbonate method for preparing the polymer of this invention is simple and convenient, in some cases products of higher molecular weight can be made by the alkali metal hydroxide method. In the alkali metal hydroxide method, described by Johnson et at., U.S. Pat. Nos. 4,108,837 and 4,175,175, a double alkali metal salt of a dihydric phenol is contacted with a dihalobenzenoid compound in the presence of a sulfur containing solvent as herein above defined under substantially anhydrous conditions.

Additionally, the polymers of this invention may be prepared by other methods known in the prior art, in which at least one dihydric phenol and at least one dihalobenzenoid compound are heated, for example, with a mixture of sodium carbonate or bicarbonate and a second alkali metal carbonate or bicarbonate having a higher atomic number than that of sodium, as described in U.S. Pat. No. 4,176,222.

The molecular weight of the poly(aryl ethers) utilized for manufacturing the devices of the instant invention is indicated by reduced viscosity data in an appropriate solvent such as methylene chloride, chloroform, N-methylpyrrolidone, and the like. The reduced viscosities of the materials, as measured at concentrations of 0.2 g per 100 ml. at 25° C., are at least 0.3 dl/g, preferably at least 0.4 dl/g and, typically, not exceeding about 1.5 dl/g.

The poly(aryl ether sulfones) employed in the practice of the instant invention have excellent transparency as well as outstanding stress-crack resistance. These devices can be steam-sterilized under stresses of 500 psi or greater and in the presence of a variety of steam boiler additives. Typical boiler additives designed to reduce corrosion in steam generating systems are amino compounds such as morpholine, hydrazine, N,N-diethylaminoethanol ("NALCO 359" or "BETZ NA-9"), and octadecylamine. Steam sterilization is also possible in the presence of various hospital cleaners and detergents, such as those sold under the tradenames of "Castle 7900" (a sonic cleaner), "Chem Crest 14" (an ultrasonic cleaner), "Tergitol Min Foam 2X" (a non ionic surfactant), and the like.

The materials of the instant invention may include pigments, thermal stabilizers, ultraviolet light stabilizers, and other additives commonly employed in the resin compounding art for such uses.

The invention will be better understood from consideration of the following examples, offered to provide specific illustration of the practice of this invention and not intended in any way to act to limit the scope of this invention.

EXAMPLES

Resins and materials employed in the following examples include:

UDEL P-1700 polysulfone: a poly(aryl ether sulfone) formed by the polycondensation of 4,4'-dichlorodiphenyl sulfone and bisphenol A. The resin, obtained from Amoco Performance Products, Inc., had a melt-flow of 6.5 g/10 minutes at 605° F. and 44 psi.

Polysulfone 1: A poly(aryl ether sulfone) of 4,4'-dichlorodiphenyl sulfone, and 4,4'-biphenol.

Polysulfone Blend: A blend (60:40 by weight) of Polysulfone 1 and UDEL P-1700 polysulfone.

Copolysulfone: Copoly(aryl ether sulfones) from 4,4'-dichlorodiphenyl sulfone 4,4'-biphenol and 4,4'-dihydroxydiphenyl sulfone at four levels of 4,4'-dihydroxydiphenyl sulfone. The compositions are given in Table 2.

PES A poly(aryl ether sulfone) from 4,4'-dichlorodiphenyl sulfone and 4,4'dihydroxydiphenyl sulfone.

EXAMPLE 1 and COMPARISON EXAMPLES A–C

Test specimens were obtained by molding the resin into 0.125 inch flex bars (5 inch by 0.5 inch). These bars were autoclaved under constant stress applied via the weighted cantilever beam method. A Pelton and Crane tabletop autoclave was employed, using a 50 ppm aqueous morpholine solution. Each cycle comprised a steam cycle of 30 minutes at 270° F under 27 psi, followed by a cooling cycle of a minimum of 10 minutes at room temperature. The cooled samples were examined for the presence of any defects, cracks, breakages, etc. The results are summarized in Table I.

TABLE I
Steam Sterilization Using a 50 ppm Aqueous Morpholine Solution

| Example | Poly(Aryl Ether Sulfone) | Stress (psi) | Cycles |
|---|---|---|---|
| Comparison A | UDEL P-1700 | 1000 | 79 (fail) |
|  |  | 500 | 148 (fail) |
|  |  | 0 | 400 |
| Comparison B | Blend | 1000 | 107 (fail) |
|  |  | 500 | 476 (fail) |
|  |  | 0 | 1012 |
| Comparison B (repeated) | Blend | 1000 | 185 (fail) |
|  |  | 500 | 1005 (fail) |
|  |  | 0 | 1012 |
| Example 1 | Polysulfone 1 | 1000 | 1320 |
|  |  | 500 | 1320 |
|  |  | 0 | 1320 |

It will be seen that Polysulfone 1, a poly(aryl ether sulfone) according to the instant invention, displays steam sterilizability under stresses of 500 psi or greater, in the presence of morpholine. The lack of reproducibility in the 500 psi strain for the two blends tested in Table I may reflect lack of uniformity in the blend.

EXAMPLES 2–5 and COMPARISON C.

In the following examples, test specimens of Polysulfone 1, Copolysulfones having the indicated compositions of diphenolic components and PES were prepared and autoclaved substantially as for Example 1.

TABLE II
Steam Sterilization of Copolysulfones

| Example | 4,4'-biphenol mole % | 4,4'-dihydroxydiphenyl sulfone, mole % | Cycles |
|---|---|---|---|
| 1 | 100 | 0 | 1000 - no visible change |
| 2 | 95 | 5 | 1000 - no visible change |
| 3 | 90 | 10 | 1000 - no visible change |
| 4 | 85 | 15 | 1000 - no visible change |
| 5 | 80 | 20 | 1000 - no visible change |
| D | 0 | 100 | 45 - cracks, ruptured |

It will be again apparent that the compositions according to the invention are autoclavable repeatedly without undergoing failure due to stress cracking, while the PES poly(ether sulfone) having no biphenyl component undergoes catastrophic failure in only 45 cycles.

Detergent and Cleaner Resistance Testing

The effect of cleaners and detergents was compared using a test run at 180° F for 24 hours using ⅛ inch bars made from UDEL P-1700 and from the other poly(aryl ether sulfones). Aqueous solutions of various cleaners and detergents were utilized. The stress was applied by bending the bar (constant strain). Note that the stress values were calculated for room temperature; therefore, their actual values may be lower at 180° F. The data are summarized in Table III. The data of Table II clearly show that Polysulfone I according to the invention performed much better than UDEL P-1700 polysulfone.

TABLE III
Effect of Various Cleaners and Detergents

| Reagent | Stress Level | UDEL P-1700 | Polysulfone 1 |
|---|---|---|---|
| Castle 7900 | 0 | Surface Cracks | OK |
| Sonic Cleaner | 1000 | TD* Cracks | OK |
| (2 oz/gal) | 2000 | Rupture | OK |
|  | 4000 | Rupture | OK |
| Chem Crest 14 | 0 | OK | OK |
| Ultrasonic | 1000 | TD* Cracks | OK |
| Cleaner | 2000 | Rupture | OK |
| (2 oz/gal) | 4000 | Rupture | OK |
| Tergitol Min | 0 | OK | OK |
| Foam 2X | 1000 | Rupture | OK |
| Monionic | 2000 | Rupture | OK |
| Surfactant** | 4000 | Rupture | OK |
| (5 ml/liter) |  |  |  |

*TD = transverse direction
**Produced by Union Carbide Corporation. The formula is $C_{12-14}H_{25-29}O(CH_2CH_2O)X[CH_2CH_2O/CH_2CH(CH_3)O]yCH_2CH(CH_3)OH$; Molecular weight is about 640; and x and y are 1 or greater.

The invention will thus be seen to be an autoclavable article comprising a poly(aryl ether sulfone) capable of withstanding 1000 cycles of steam sterilization at a stress level of at least 500 psi for at least 1000 cycles, when the autoclaving is conducted at 270° F. under a pressure of 27 psi using aqueous morpholine at a concentration of 50 ppm. The poly(aryl ether sulfone) may be further described as consisting of from 40 to 0 mole %, preferably from about 20 to about 0 mole % of the structural unit:

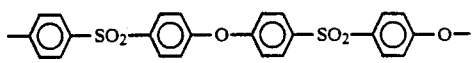

and, correspondingly, from about 60 to about 100 mole %, preferably from about 80 to about 100 mole % of the structural unit:

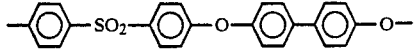

The article may take the form of an autoclavable tray or container for medical use.

We claim:

1. An autoclavable container comprising a poly(aryl ether sulfone) capable of withstanding at least 1000 cycles of steam sterilization at a stress level of 500 psi without stress-crack failure, said steam sterilization cycle conducted for 30 min. at 270° F. and 27 psi using aqueous morpholine at a concentration of 50 ppm, said poly(aryl ether sulfone) consisting of from 60 to about 100 mole % of the structural unit:

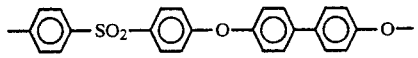

and, correspondingly, from 40 to 0 mole % of the structural unit:

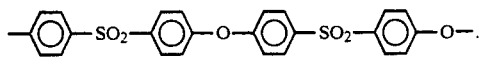

with the proviso that no other structural units are present.

2. The container of claim 1 wherein said poly(aryl ether sulfone) consists of from about 80 to about 100 mole % of the structural unit:

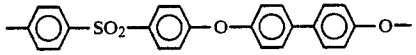

and, correspondingly, from 20 to 0 mole % of the structural unit:

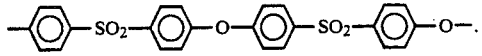

3. An autoclavable package comprising medical instruments and a container comprising a poly(aryl ether sulfone) capable of withstanding at least 1000 cycles of steam sterilization at a stress level of 500 psi without stress-crack failure, said steam sterilization cycle conducted for 30 min. at 270° F. and 27 psi using aqueous morpholine at a concentration of 50 ppm, said poly(aryl ether sulfone) consisting of from 80 to about 100 mole % of the structural unit:

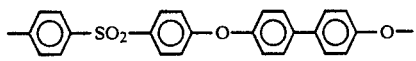

and, correspondingly, from 20 to 0 mole% of the structural unit:

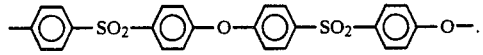

with the proviso that no other structural units are present.

* * * * *